United States Patent [19]

Horiba et al.

[11] Patent Number: 4,740,896
[45] Date of Patent: Apr. 26, 1988

[54] X-RAY CT SYSTEM WITH MEANS TO EXPAND DETECTOR SIGNALS BY INTERPOLATION BEFORE FILTER PROCESSING IS PERFORMED

[75] Inventors: Isao Horiba; Akira Iwata, both of Aichi; Hiroshi Sasaki, Ibaraki; Kazuhiro Sato, Chiba, all of Japan

[73] Assignee: Hitachi Medical Corporation, Japan

[21] Appl. No.: 776,473

[22] Filed: Sep. 16, 1985

[30] Foreign Application Priority Data

Sep. 19, 1984 [JP] Japan ................................. 59-194768

[51] Int. Cl.⁴ ..................... G06F 15/42; A61B 6/02; G06K 9/46
[52] U.S. Cl. .................................... 364/414; 378/901; 382/54
[58] Field of Search ................. 364/414; 382/54; 278/901

[56] References Cited

U.S. PATENT DOCUMENTS

| 4,178,510 | 12/1979 | Wagner | 364/414 |
| 4,275,444 | 6/1981 | Ryan | 364/414 |
| 4,284,896 | 8/1981 | Stonestrom | 364/414 |
| 4,630,307 | 12/1986 | Cok | 382/54 |

FOREIGN PATENT DOCUMENTS 8402990 8/1984 PCT Int'l Appl. ................... 382/54

Primary Examiner—Jerry Smith
Assistant Examiner—Gail O. Hayes
Attorney, Agent, or Firm—Gerald J. Ferguson, Jr.; Michael P. Hoffman; Michael J. Foycik, Jr.

[57] ABSTRACT

In an X-ray CT apparatus including an X-ray source for irradiating X-rays to an object to be tested; a radiant ray detector for detecting the amount of X-rays transmitted through said object to be tested; a device for rotating the X-ray source and the detector about an axis to produce detection signals corresponding to the amount of transmitted X-rays; a filter for filter processing the detection signal; circuitry for back-projecting the filtering resultant to thereby reproduce a distribution image of X-ray absorption in a cross-section of the object to be tested, and a device for interpolating interpolation values into the detection signals to form expanded signals having an elongated length so that the expanded signals are used for the filter processing.

10 Claims, 15 Drawing Sheets $(T \simeq P)$

X-RAY CT SYSTEM WITH MEANS TO EXPAND DETECTOR SIGNALS BY INTERPOLATION BEFORE FILTER PROCESSING IS PERFORMED

BACKGROUND OF THE INVENTION

1. Field of the Invention

The present invention relates to an X-ray CT (computerized tomography) apparatus, and, more particularly, to an improved X-ray CT apparatus for obtaining a picture having higher space resolving power in comparison with conventional apparatus.

2. Description of the Prior Art

Generally, each detector in a detector array of an X-ray CT apparatus has a detector aperture width which cannot be neglected with respect to the width of the detector. Data sampled from the detector output train latently includes frequency components higher than the Nyquist frequency determined by the sampling interval. However, these components cannot be extracted by conventional image processing apparatus.

SUMMARY OF THE INVENTION

An object of the present invention is to provide an X-ray CT apparatus which is able to resolve a subject into its substances, the substances having a smaller component than the width of detector by the utilization of the fact that the data measured by the CT apparatus includes frequency components higher than the Nyquist frequency determined by the detector interval (sampling interval).

The object of the invention can be attained by adding interpolation values to the projection signals so that the length thereof is expanded, the interpolation values being successively obtained by detecting two sample points of the projection signals occurring at relatively facing positions, that is, at a beam generation position and a beam detector position, the two sample points being utilized to obtain the interpolation values.

DETAILED DESCRIPTION OF PREFERRED EMBODIMENT

Figure 1:
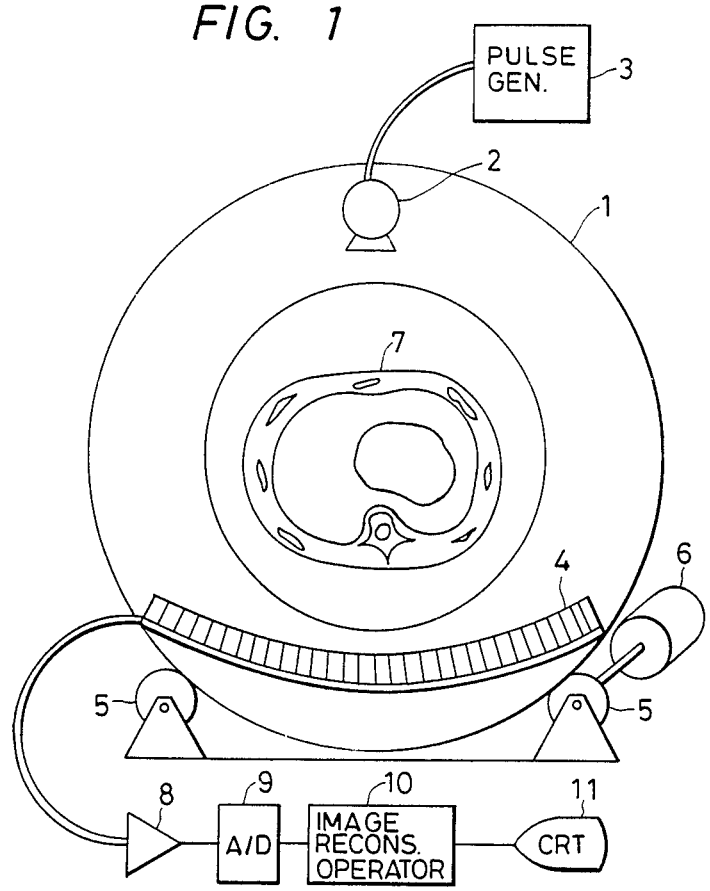
FIG. 1 is a diagram showing a conventional fan beam CT apparatus.

1. Detector Array of X-ray CT Apparatus (1) Fan Beam CT Apparatus:

FIG. 1 shows an apparatus which is now most widely used among X-ray computed tomographic apparatuses and which performs measurement only by rotational scanning by means of a fan beam.

An X-ray tube 2 and a detector array 4 which are fixed in opposition to each other on a disc 1, are rotated around an object to be tested 7 at a constant speed by supporting rollers 5 and an electric motor 6 driving the supporting rollers. The X-ray tube emits X-ray pulses generated by a high-voltage pulse generator 3 at regular intervals, and projection data passing through the object 7 fixed at the center are measured a number of times in a respective number of rotational positions of the X-ray tube and the detector array. Signals from the detector array corresponding to the plural projectional data obtained in the foregoing manner are successively applied to an amplifier 8 to be amplified therein, converted into digital signals by an analog-to-digital converter 9, and reproduced into a tomographic image by an image reconstructing operator 10. The thus obtained tomographic image is displayed on a CRT 11.

Figure 2:
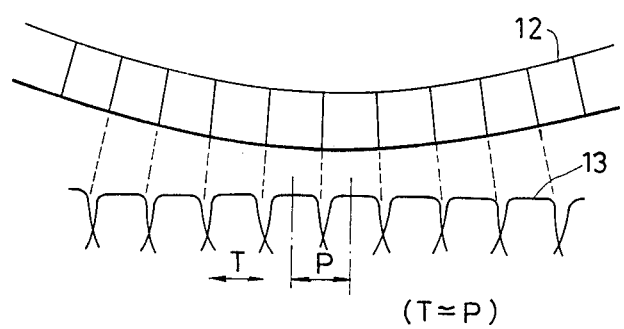
FIG. 2 is a diagram showing a detector aperture characteristic in the case where a linear detector array is used.

(2) Sampling by Means of Fan Beam Detector Array:

The reference numeral 12 in FIG. 2 designates a fan beam detector array (detector channel). The array is constituted by about 500 to 1000 detecting elements where each detecting element constitutes a scintillator containing inactive gasses and a semiconductor photosensor. The elements are mutually separated by means of "partitions" which are provided for the purpose of removing scattered X-rays between the elements.

A sample interval P shown in FIG. 2 is the distance between the respective centers of two adjacent detecting elements. The relationships between the sample interval P and the Nyquist frequency fc is expressed by the follwing equation (1).

$$fc = \tfrac{1}{2}P \qquad (1)$$

One projection datum which is measured by the detector array with the X-ray tube placed at the same position, has no frequency components higher than the Nyquist frequency determined by the equation (1).

In considering the data measured by the detector array 12, the detector aperture characteristic is important in addition to the Nyquist rate. Each detecting element detects X-rays on its photo-receiving plane having a regular area. The widthof the photo-receiving plane taken along the detector array is referred to as an aperture width T.

The width T is a value obtained by substracting the width of the above-mentioned "partition" from the sample interval P. The distribution of sensitivity on the photo-receiving plane of the detector is called the detector aperture characteristic. The reference numeral 13 in FIG. 2 indicates the detector aperture characteristic taken along the aperture width.

(3) Relationship between Detector Aperture Characteristic and Observed Waveforms:

Apart from the CT apparatus per se, the detector aperture characteristic will be generally explained hereunder.

Figure 3:
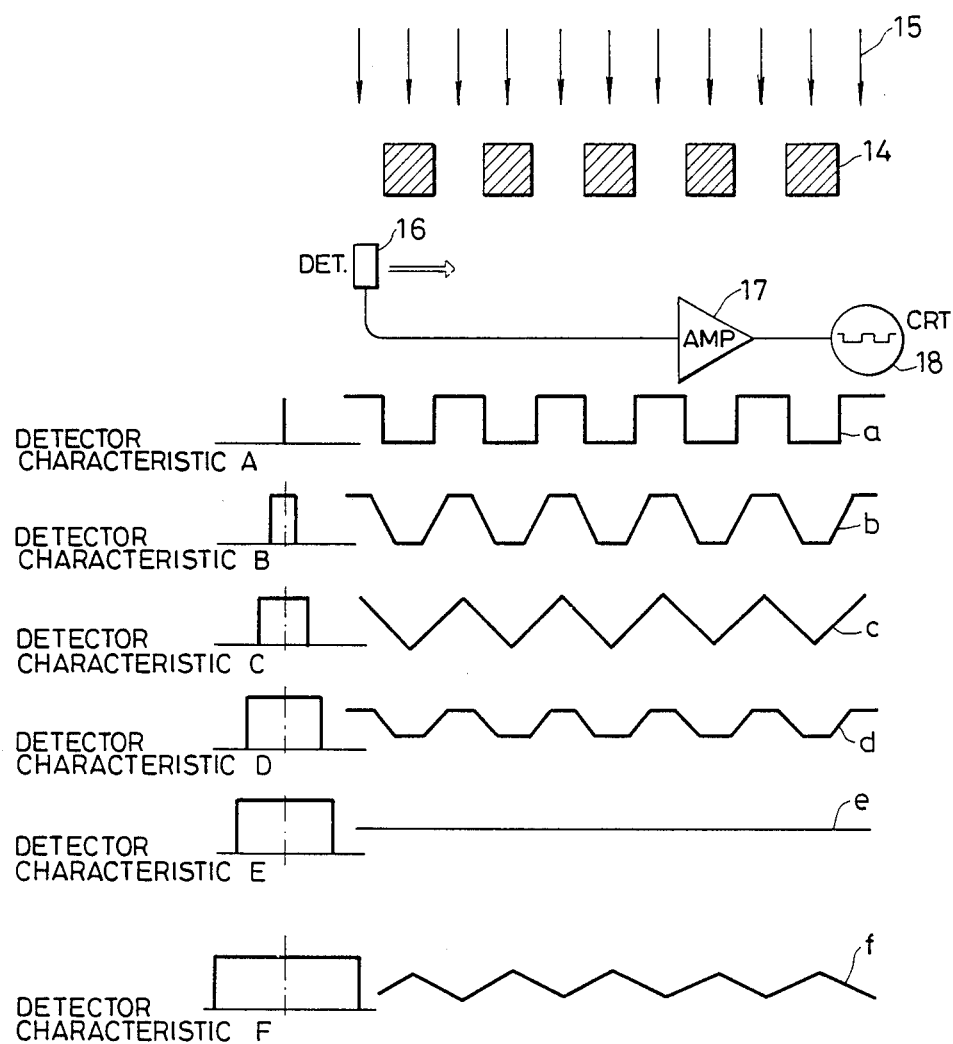
FIG. 3 is a diagram showing a detector aperture characteristic and observed waveforms associated therewith.

FIG. 3 shows the relationship between the detector aperture characteristic and the observational waveform in the case of making observations of the shape of the object to be tested by using light, electromagnetic waves such as X-rays and γ-rays, or ultrasonic waves. In FIG. 3, square absorbers 14 are irradiated with X-rays 15 and scanned rightward as indicated by the arrow in the drawing at a constant speed by a detector 16 provided opposite to the absorbers 14. A signal current from the detector 16 is amplified by an amplifier 17, and the shapes of the absorbers are observed on a cathode ray tube (CRT) 18 as a time series signal. In the example shown in FIG. 3, the square absorbers 14 are disposed at intervals of the same length as one side of the square and, accordingly, small electric signals passing through the absorbers 14 and large electric signals not passing through the absorbers 14 are alternately observed on the CRT 18. The waveforms a–f show the shape of the object to be tested as the respective results measured by six kinds of detectors A–F having photo-receiving planes different in area respectively, it being assumed that the photo-receiving plane of each of the detectors has a uniform distribution of sensitivity.

The detector of the detector aperture characteristic A has a sufficiently small area as compared with the absorber. When measured by this detector, a square waveform a is observed. The detector of the detector characteristic B has an area about half as large as the absorber. When measured by this detector, a trapezoidal waveform b is observed. As the detector becomes large in size, the waveform has its flat portions reduced and if the detector becomes about as large as the absorber, as shown with the detector characteristic C, the waveform becomes triangular. When the detector is made further larger, the waveform becomes trapezoidal again as shown in a waveform d while its amplitude is reduced. When the detector becomes twice as large as the absorber, the amplitude becomes zero and, as shown in a waveform e, the shape of the absorber is not observed in spite of the movement of the detector. When the detector becomes further larger as shown in the detector characteristic F, that is, when the detector becomes three times as large as the absorber, the shape of the absorber is observed as a triangular waveform again, while as compared with waveform c, the waveform f is small in amplitude and reverse in phase.

As shown in the foregoing examples, the actually observed waveforms are different depending on the detector aperture characteristic (aperture function). These phenomena can be made clear by the representaton on a frequency axis as shown in FIG. 4.

Figure 4A:
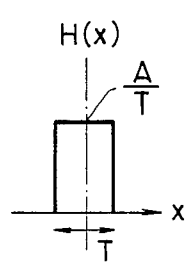
FIGS. 4A and 4B are a diagram showing a detector aperture characteristic and its associated frequency characteristics.

In FIG. 4 h(x) of FIG. 4A designates generally a typical detector aperture characteristic. The size of the light receiving portion of the detector is designated by T, and the sensitivity, which is uniform on the photo-receiving plane, is designated by A/T. The detector has such a characteristic expressed as follows.

$$h(x) = A/T \quad -T/2 \leq x \leq T/2 \qquad (2)$$
$$O \qquad x < -T/2 \text{ or } x > T/2$$

The frequency characteristic of this detector is obtained by Fourier transform by the formula (2). The result is as follows.

$$H(\omega) = \int_{-\infty}^{\infty} h(x)e^{-j\omega x} \qquad (3)$$

$$dx = \frac{A \sin(T\omega/2)}{(T\omega/2)}$$

Figure 4B:
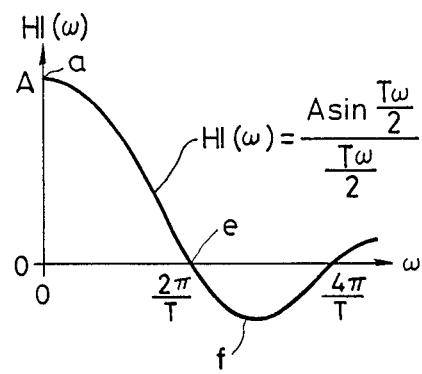

The function of the formula (3) is called a sync function. In the waveform, as shown in FIG. 4b, the gain is A at the frequency of zero, decreases with the increase of frequency, becomes zero at the frequency of $2\pi/T$, and then becomes negative.

The points a, e, and f of FIG. 4 correspond to the response waveforms a, e, and f of FIG. 3 respectively. The point e where the response waveform becomes zero in FIG. 3, is the point at the frequency of $2\pi/T$ in FIG. 4. Therefore, the smaller the aperture T of the detector is, the higher the frequency becomes for the signal transmission in a positive phase.

(4) Frequency Characteristic of CT Fan Beam Detector Array:

Returning again to the fan beam detector array of FIG. 2 each of the detecting elements has an aperture characteristic of nearly square width T as designated by the reference numeral 13. The detecting elements are disposed at regular intervals P as described above, and the relationship between the aperture transmission characteristic in one projection data measured by this detector array and the Nyquist frequency is as shown in FIG. 5.

Figure 5:
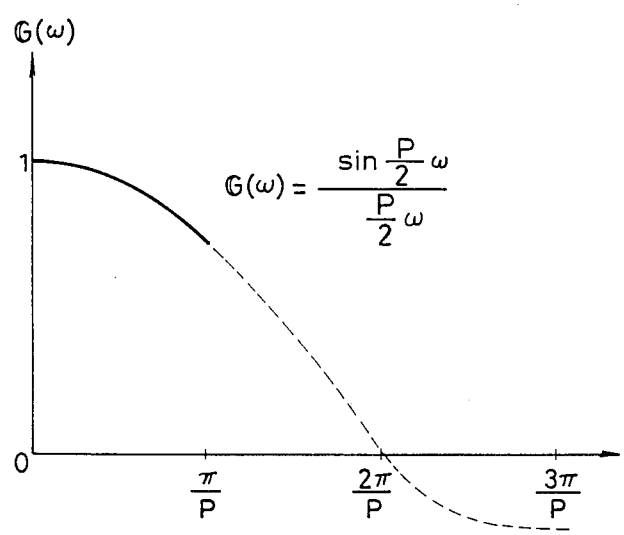
FIG. 5 is a diagram showing the relationship between a detector aperture transmission characteristic and the Nyquist frequency in the case where a linear detector array is used.

FIG. 5 shows the results obtained such that the detector aperture characteristic has been transformed into frequency components while approximating the detector aperture characteristic to square.

The detector aperture characteristic in the example of FIG. 2 is under the condition tP, and at this time, the aperture transmission characteristic G(ω) is approximated as follows by using the formula (3):

$$G(\omega) = \frac{\sin(P/2)\omega}{(P/2)\omega} \quad (4)$$

The aperture transmission characteristic becomes zero at the frequency of ω=2π/P, and at the frequencies higher than this value there occurs back in phase while at the frequencies lower than this value, transmission occurs in a positive phase. In FIG. 5, the solid line in FIG. 5 shows a range of frequency lower than the Nyquist frequency (π/P) in one projection datum, while the broken line shows the aperture transmission characteristic at the frequency higher than the Nyquist frequency. The portion shown by the broken line corresponds to a portion of occurrence of turn-over noise in the one projection datum.

Although FIG. 5 shows the case where the upper limit of the range of positive transmission is just twice the Nyquist frequency, this is the example where the range of positive phase transmission is the narrowest in the case of a CT fan beam detector array. If the "partition" provided between the detecting elements has a considerable width, the in equality $$T < P \quad (5)$$

is satisfied and the upper limit of the range of positive phase transmission has the value that satisfies the equality $$\omega = 2\pi/T \quad (6)$$

Compared with the Nyquist frequency having a value that satisfies the following equation $$\omega_1 = \pi/P \quad (7),$$

the upper limit of the range of positive phase transmission has a value twice as high as the Nyquist frequency or more.

(5) Flow of Data in the Case where Data Measured by Fan Beam Detector Array are Reconstructed According to Filter Correction reverse Projection:

Reconstructive operation is performed on the projection data by the image reconstructing operator 10 of FIG. 1. There have been employed many of algorithms to implement image reconstruction, such as two-dimensional Fourier transform, filter correction back projection, etc. Filter correction back projection has been used most widely among those algorithms.

Figure 6A:
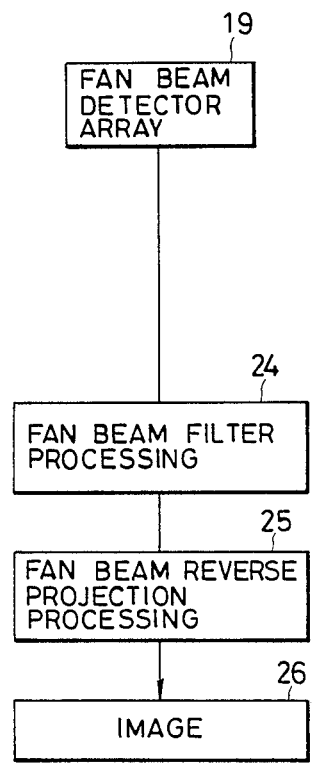
FIGS. 6A and 6B are diagrams showing conventional methods for reconstruction of data measured by a fan beam detector array.
Figure 6B:
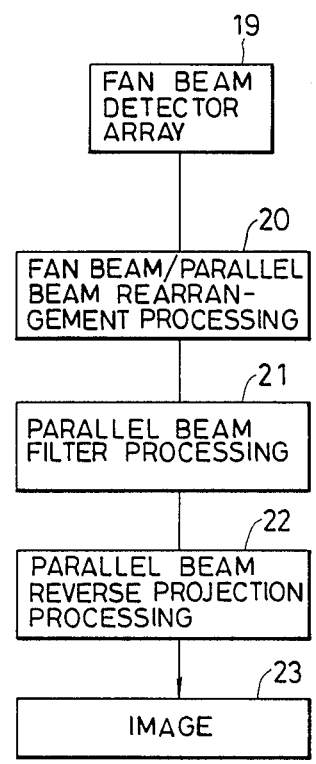
Figure 7:
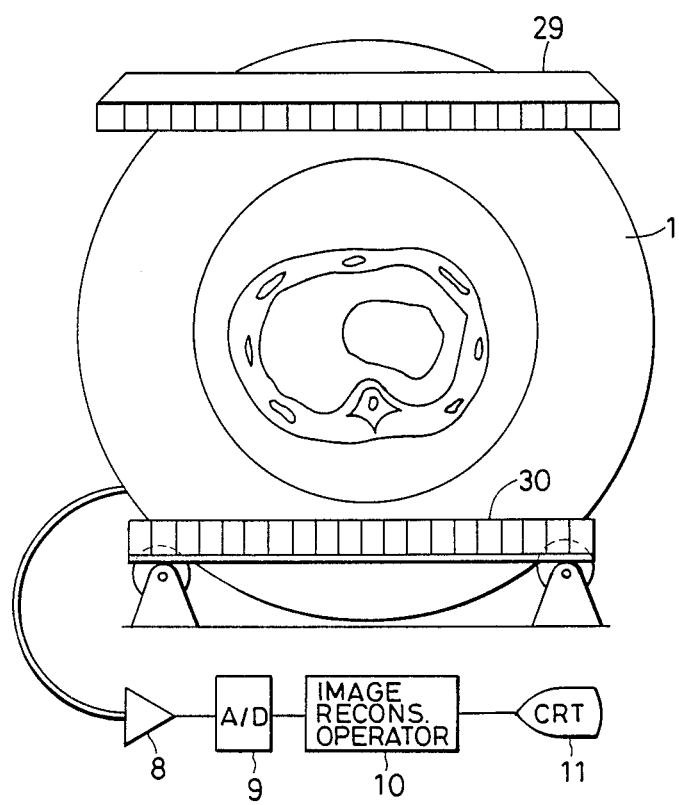
FIG. 7 is a diagram showing a conventional CT apparatus having a parallel beam detector array.

In the case where the data measured by the fan beam detector array 4 of FIG. 1 are reconstructed by the filter correction back projection, two kinds of algorithms shown in FIGS. 6A and 6B are basically implemented. According to the algorithm of FIG. 6B, a data group which may be obtained when parallel beams emitted from an X-ray tube array 29 (FIG. 7) disposed on a straight line are measured by parallel beam detector array 30 as shown in FIG. 7, is produced by a fan beam/parallel beam rearranging unit 20 on the basis of a data group measured by a fan beam detector array 19, and the thus produced data group is transferred to a parallel beam filter processing unit 21, and a parallel beam back projection processing unit 22, thereby obtaining an image 23.

According to the algorithm of FIG. 6A, on the other hand, the data measured by the fan beam detector array 19 is directly transferred to a fan beam filter processing unit 24 and a fan beam back projection processing unit 25 without performing rearrangement of the data, thereby obtaining an image 26.

Figure 8:
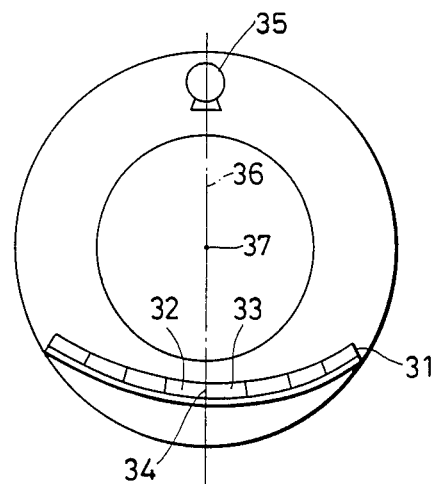
FIG. 8 is a diagram showing a conventional CT apparatus having a fan beam detector array without shifting.

(6) Setting up Detector Array with Shifting by ¼ of Detector Width:

FIG. 8 shows typically the positional relationship between a fan beam detector array 31 with a center of rotation 37 in an ordinary CT apparatus with no shifting. In this apparatus, the detector array 31 is set up such that the broken line 36 joining the center of an X-ray tube 35 with the center of "partition" 34 between two central detecting elements 32 and 33 in the detector array 31 passes through the rotational center in the measuring operation.

Figure 9:
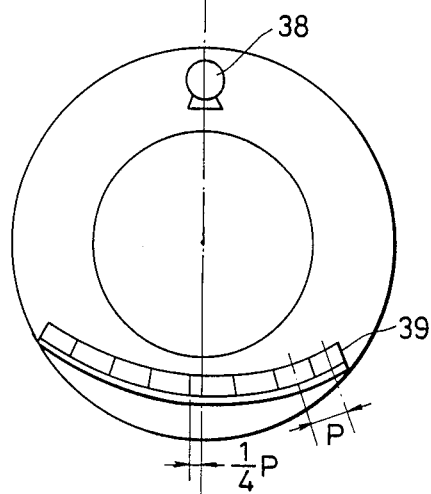
FIG. 9 is a diagram showing a conventional CT apparatus having a fan beam detector array with shifting.

In a CT apparatus shown in FIG. 9, on the other hand, a detector array 39 is set up with a left shift by a length of ¼ of the sample interval P. Although FIG. 9 shows the case where the detector array is shifted left, the shifting may be to the right. A detector array with a shift by a length of ¼ of a detector width will be referred to as "a detector array with shifting" hereinafter.

Figure 10:
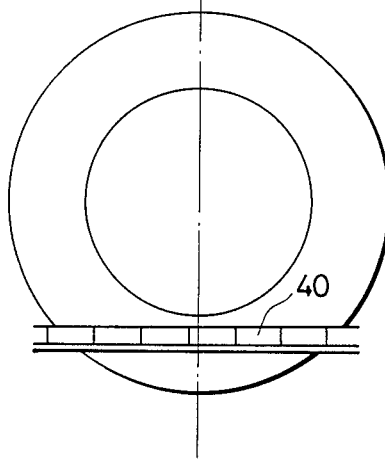
FIG. 10 is a diagram showing a conventional CT apparatus having a parallel beam detector train with shifting.

FIGS. 8 and 9 show CT apparatuses each having a fan beam detector array, in which measured data over 360° can be rearranged to data measured over 360° by a parallel detector array by the fan beam/parallel beam rearrangement as shown in FIG. 6B. The fan beam/parallel beam rearranging unit may also arrange data measured by a fan beam detector array with shifting as shown in FIG. 9 into data measured by a parallel beam detector array 40 with shifting as shown in FIG. 10.

Figure 11A:
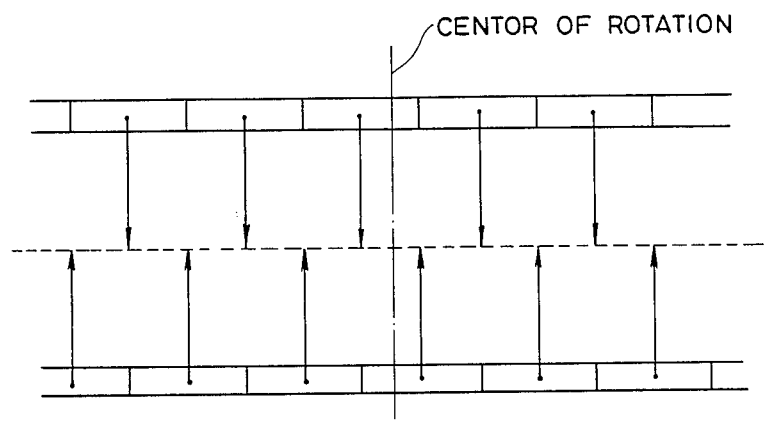
FIGS. 11A and 11B are diagrams showing the positional relationships of opposing parallel beams in parallel beam detector arrays with and without shifting, respectively.
Figure 11B:
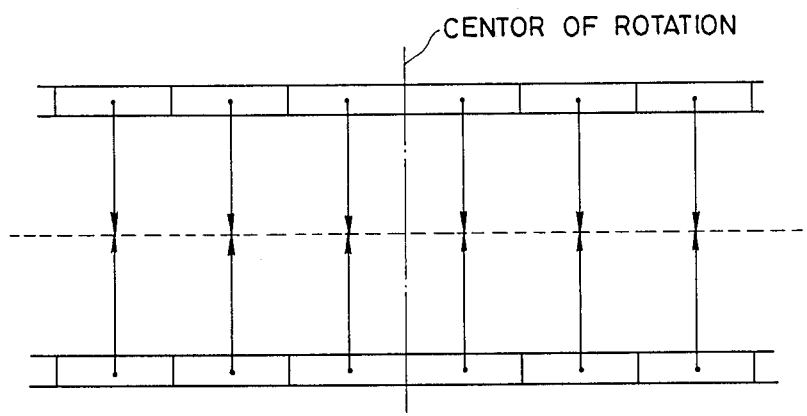

FIG. 11A shows the condition where a pair of data measured at positions separated by 180° by a parallel beam detector array with shifting are arranged with respect to the position of the rotational center. Since each of the detector arrays has a shift of ¼ of the detector width, the relative shift between the detector arrays becomes ½ of the detector width. This positional relationship is not changed even if filter processing is performed. In back projecting, the data after filter processing are accumulated on an one or two dimensional memory with such a positional relationship that the center of the respective detector aperture and the center of corresponding detector aperture of the opposite detector array are mutually interpolated. Without shifting, as can be seen in FIG. 11B, opposite data is reversely projected onto the same position. One of the two mutually opposite data becomes, therefore, redundant. In comparing FIGS. 11A and 11B with each other, it can be seen the former has a larger quantity of information than the latter.

2. Image Reconstructing Algorithm for Obtaining High Resolution Image (1) Theory for High Resolution:

In a data group measured by the parallel detector array with shifting, data at intervals of 180° are parallel with each other and mutually linearly shifted by the length of ½ of detector width as shown in FIG. 11A. This property can be utilized to obtain high resolution.

Figure 12:
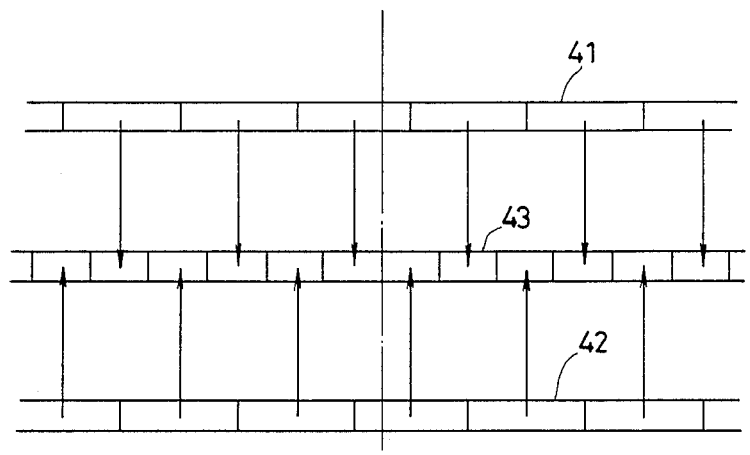
FIG. 12 is a diagram showing a method of expanding data in accordance with one embodiment of the invention, wherein two sets of data measured at opposing positions by a parallel detector array with shifting are alternately stored in a linear or one-dimensional buffer memory.
Figure 24:
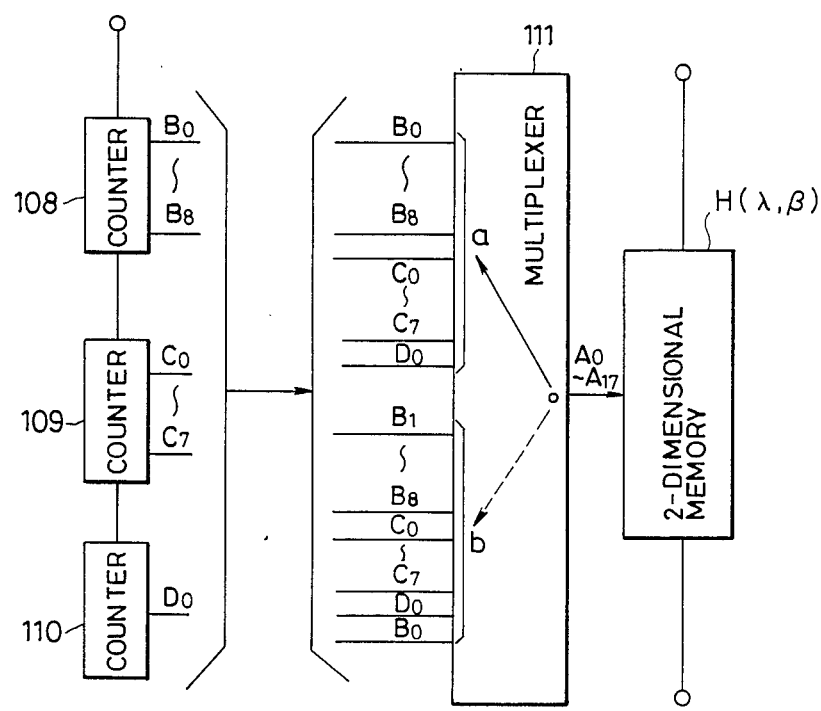
FIG. 24 shows an example of a circuit for obtaining a expanded data.

FIG. 12 shows processing for obtaining enlarged data 43 in such a manner that a pair of data 41 and 42 measured at mutually opposite positions are taken out of a data group measured by the parallel detector array with shifting, the data 41 and 42 are arranged with respect to the position of the rotational center, and the data 41 and 42 are put alternately in a linear buffer memory, such as memory 86 as will be explained below with respect to FIG. 22. This process is implemented by a circuit as illustrated in FIG. 24, and the expanded data can be obtained. Counter 108, 109 and 110 are cascade-connected so that when all bits of the counter 1 are chaged to qero level, the counter 108 supplies the counter 109 with a first carry signal, and when all bits of the counter 109 are changed to zero level, the counter 109 supplies the counter 110 with a second carry signal. The outputs of the counters 108, 109 and 110 are applied through a multiplexesr 111 to a two-dimensional memory 112 as an address signal. The multiplex is designed to alter the line arrangement of the outputs of the counter 108, 109 and 110. When a measured data is written into the two-dimensional memory 112 in FIG. 24, the multiplexer 111 selects a-lines as illustrated in FIG. 24, and the outputs of the counter 108, 109 and 110 are sequentially applied to input terminals of the two-dimensional memory 112, from the smallest value of the counter 108, 109 and 110 to the largest value.

When the measured data is read out from the two-dimensional memorey 112, the multiplexesr selects b-lines, and at this time, the least significant bit ($B_0$) of each of the counters 108, 109 and 110 is connected to the most significant bit ($A_{17}$) of the two-dimensional memory 112. For example, the counters 108, 109 and 110 are nine-bit counter, eight-bits counter, and one-bit counter, respectively, $\lambda$ is 512, and $\beta$ is 512, where $\lambda$ is the number of detector elements, and $\beta$ is the number of samplings in the direction of the rotatoin of the detector elements. In the case of writing, the measured data is written into the two-dimensional memory 112 in the order shown below: H(0,0), H(1,0), H(2,0), . . . , H(511,0), H(0,1), H(1,1), . . . , H(511,1), H(0,2), H(1,2), . . . , H(511,255), . . . , H(511,511). where H($\lambda,\beta$) is a measured projection data. In the case of reading, the measured data is read out from the two-dimensional memorey in the order shown below: H(0,0), H(0,256), H(1,0), H(1,256), . . . , H(511,0), H(511,256), H(0,1), H(0,257), . . . , H(511,255), H(511,511). If this processing is performed as to the whole data over 360°, the number of data is reduced to half, that is over 180°.

Figure 13:
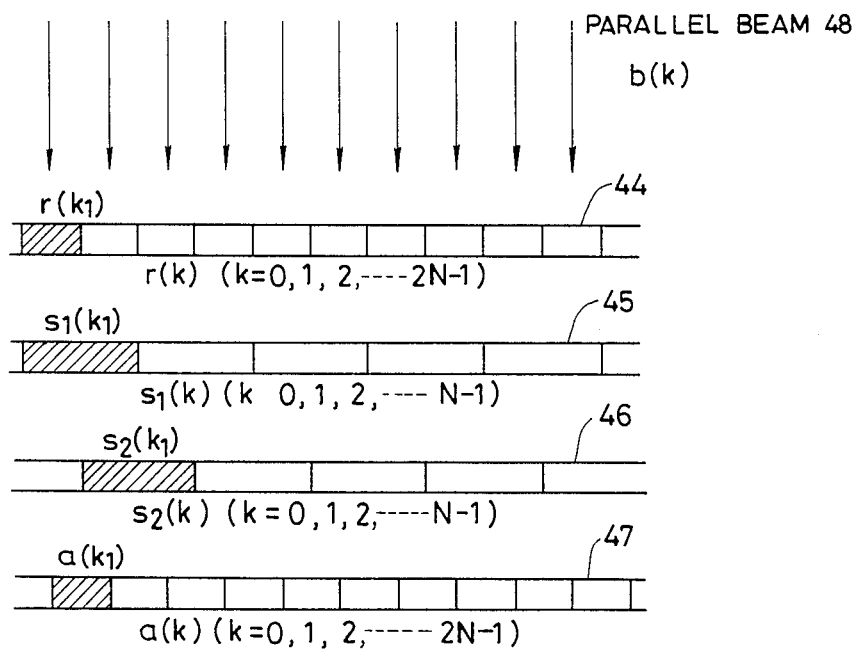
FIG. 13 is a diagram showing an example of checking data expanded by a data expanding method of the present invention in which shifting of the detector array is utilized.

What kind of property is provided in the enlarged data 43 made by the processing of FIG. 12 will not be discussed. The reference numeral 44 (FIG. 13) designates a parallel beam detector array which is half of the detector array shown by the reference numerals 41 and 42 of FIG. 12 in detector width (sample interval) and in detector aperture width. The reference numerals 45, 46 and 47 designate the same ones designated by the reference numerals 41, 42 and 43 in FIG. 12 respectively. In those designated by the reference numerals 44, 45 and 46, however, the detector aperture width is regarded to be equal to the sample interval. The reference numeral 48 designates a group of parallel beams coming perpendicularly to the parallel detector arrays from the upper portion in FIG. 13 when those designated by the reference numerals 44, 45 and 46 are disposed in the positions as shown in FIG. 13. Those designated by the reference numerals 44, 45, 46, 47 and 48 are now expressed by one-dimensional matrices r(k), s1(k), s2(k), a(k) and b(k). That is, the data measured by the parallel beam detector array of half detector width is expressed by the matrix r(k)(k=0, 1, 2, . . . 2N−1), the pair of data measured by the parallel beam detector arrays with shifting are expressed by the matrices s1(k=0, 1, 2, . . . N−1)

s2(k=0, 1, 2, . . . M−1), and the composite data made from s1 and s2 by the processing of FIG. 12 is expressed by the matrix a(k)(k=0, 1, 2, . . . 2N−1).

The positional relationship of r, s1, s2 and a with respect to the same data number k1, is shown in the hatched portions in FIG. 13. The incident parallel beam group is regarded as forming one-to-one correspondence to r(k) and expressed by b(k) (k=0, 1, 2, . . . 2N−1). At this time, however, b(k) is a parallel beam having the width as shown in FIG. 16a. This width is constant until the beam reaches a detecting element from a corresponding X-ray tube as indicated in FIG. 12. In particular, the width is equal to the aperture width of the detecting element constituting the detector array 44 of FIG. 13. That is, $$r(k) = b(k) \tag{8}$$

The pair of detector arrays 45 and 46 with shifting of FIG. 13 detect the parallel beam group 48 respectively in such a manner as follows:

$$s1(k) = b(2k-1) + b(2k) \tag{9}$$

$$s2(k) = b(2k) + b(2k+1) \tag{10}$$

From the equations (8), (9) and (10), the following equations (11) and (12) can be obtained:

$$s1(k) = r(2k-1) + r(2k) \tag{11}$$

$$s2(k) = r(2k) + r(2k+1) \tag{12}$$

The equations (11) and (12) show the relations among those designated by 44 to 45 and 46.

The relationship of those designated by 45 and 46 to that designated by 47, that is, the relationship of s1 and s2 to a is shown in FIG. 12, and this relationship can be expressed by the following equations (13) and (14):

$$a(2k-1) = s1(k) \tag{13}$$

$$a(2k) = s2(k) \tag{14}$$

Substituting the equations (11) and (12) for the equations (13) and (14).

$$a(2k-1) = r(2k-1) + r(2k) \tag{15}$$

$$a(2k) = r(2k) + r(2k+1) \tag{16}$$

Rewriting 2k into k, the equations (15) and (16) are united into the following equations (17):

$$a(k) = r(k) + r(k+1) \tag{17}$$

In comparing r with a, as to the same data number k1, the position or a is shifted right by ½ of the virtual detector width regardless of the shifting direction. This is shown by the hatching in FIG. 13.

The equation (17) shown that data a is the blurred one of data r. That is, data a is obtained by periodic convolution of data r and an two-point adding operator h shown in FIG. 14.

$$a = r * h \tag{18}$$

Figure 14:
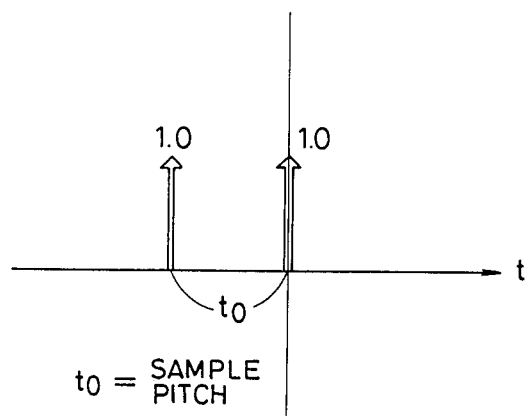
FIG. 14 is a diagram for explaining a two-point adding operator h used in the present invention.

The sign * is an operator designating the periodic convolution. In FIG. 14, $t_O$ designates the detector width and two-point adding operator h is obtained by the linear sum of delta functions $\delta(\tau)$ and $\delta(t-t_O)$ in a continuous space. That is, the equation $$h(t) = \delta(\tau) + \delta(t - t_O) \tag{19}$$

expresses the two-point adding operator h. At this time, Fourier transform H of h is expressed as follows:

$$H(\omega) = 1 + e^{-j\omega t O} \tag{20}$$

Assuming the Fourier transforms of a and r are A and R respectively, the convolution integral in a real space is equivalent to the product in a frequency space. According to the equation (18), $$A = H \cdot R \tag{21}$$

is established. Moreover, according to the equation (21), $$R = A/H \tag{22}$$
$$= H^* A$$

is derived, where H* is as follows:

$$H^* = \frac{1}{H} = \frac{1}{1 + e^{-jt0}} = \frac{1 + e^{j\omega t0}}{(1 + \cos\omega t_0)^2 + (\sin\omega t_0)^2} \tag{23}$$

$$= \frac{1 + e^{j\omega t0}}{2 + 2\cos\omega t_0} = \frac{1}{2}\left(1 + j \cdot \frac{\sin\omega t_0}{1 + \cos\omega t_0}\right)$$

Figure 15:
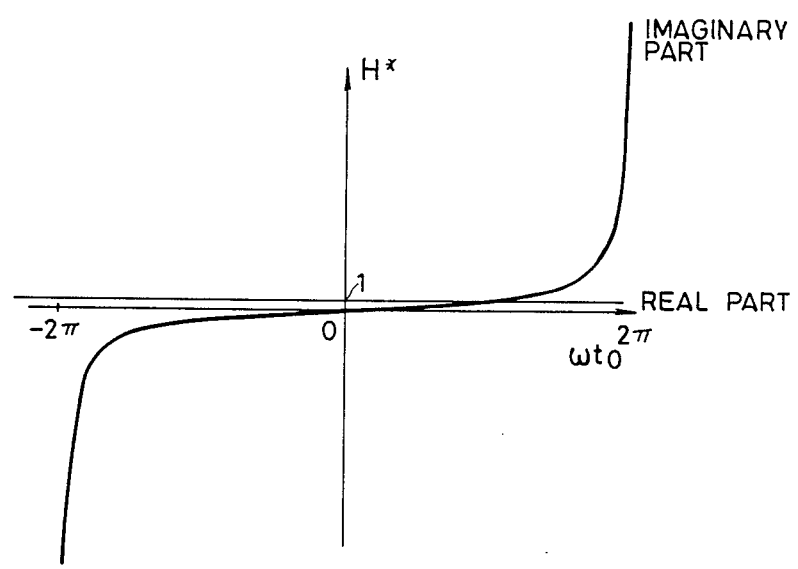
FIG. 15 is a characteristic graph of an ideal 2fc blur correction filter $H^*(\omega)$.

H* is shown in FIG. 15.

The equation (22) means that there is obtained one data equivalent to the data measured by the parallel detector arrays in which the detecting elements, having the detector width of ½ of the actual detecting elements designated by the reference numeral 44 in FIG. 13, are arranged at intervals of ½ of the actual sample intervals, through the steps of (a) performing a Fourier transform of the data obtained by making one expanded data from opposite data throughout the whole data in the manner as shown in FIG. 12 in a parallel beam data group obtained by performing fan beam/parallel beam converting processing on the data group measured by the CT apparatus in which detector arrays composed of many detecting elements having the detector width approximately equal to the sample interval are mounted with shifting by ¼ of the sample interval as shown in FIG. 9; (b) multiplying the data subjected to the Fourier transform by the function H* expressed by the equation (23); and (c) returning the thus multiplied data to real space.

When an image is reconstructed by the filter correction back projection by using this resultant data, the special resolution power is increased by about twice (that is, it is possible to resolve the image into small ones of about ½) as compared with the conventional reconstructing method.

Figure 16:
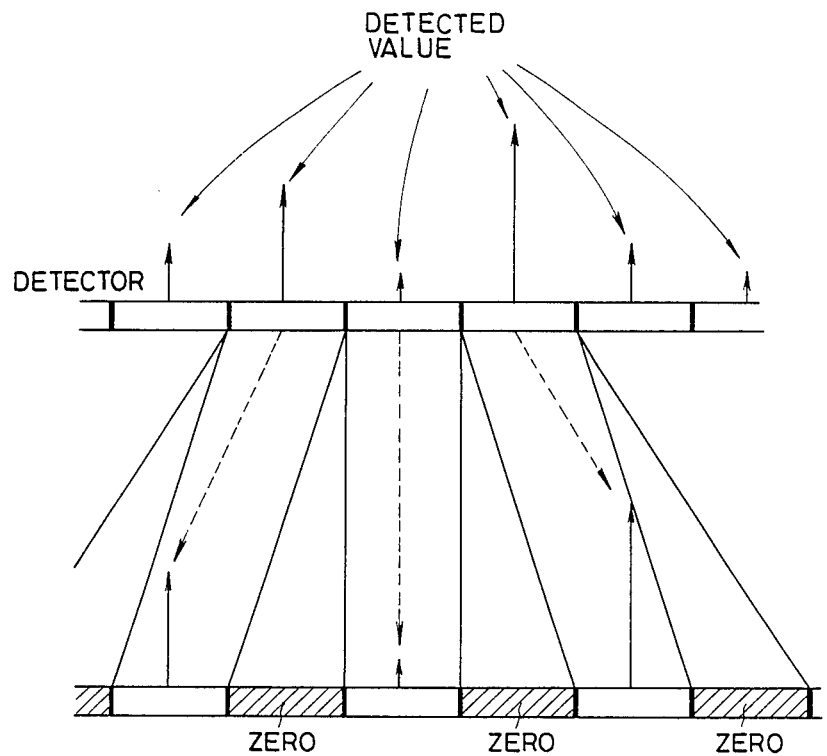
FIG. 16 is a diagram showing an expansion method for the expansion of data by zero-insertion in accordance with another embodiment of the invention.

(2) Data Expanding method by Zero Interpolation:

There is another method to attain the result equivalent to the algorithm as described above in the item 2, (1) without performing the processing shown in FIG. 12. In this method, zero interpolation as shown in FIG. 16 is performed as a data expanding method for the data measured by the parallel detector arrays with shifting. The data length is expanded twice by the interpolation of zero between mutually facing detected values.

Figure 17:
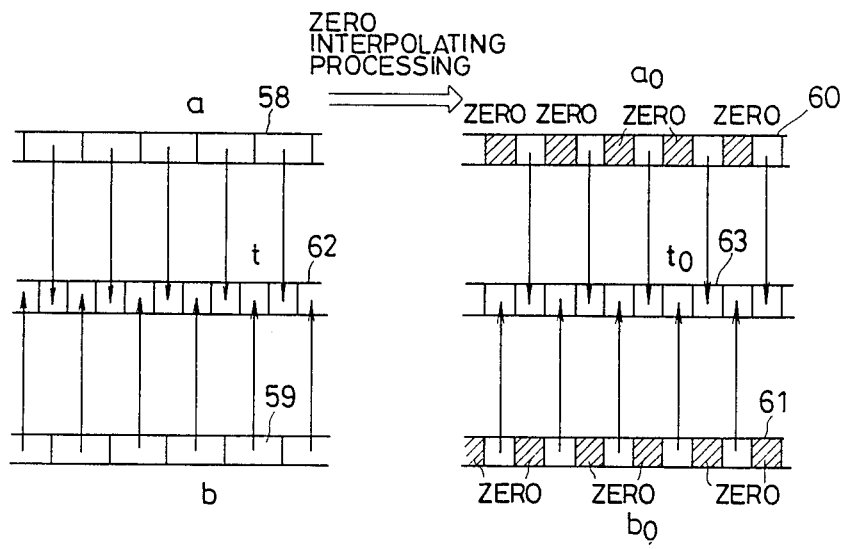
FIG. 17 is a diagram showing a comparison between the processing in FIG. 12 and the processing of FIG. 16.

FIG. 17 is used to explain that the method of making one composite data from two opposite data as shown in FIG. 12 and the method of zero interpolation as shown in FIG. 16 are equivalent in the data expanding processing for data measured by parallel detector arrays with shifting. The reference numerals 58 and 59 designate a pair of data measured at an interval of 180° by the parallel detector arrays with shifting. The reference numeral 62 designates expanded data produced from the pair of data 58 and 59 by the processing shown in FIG. 12. The reference numerals 60 and 61 designate data after zero interpolation processing on the data 58 and 59. The reference numeral 63 designates expanded data obtained by the addition of the data 60 and 61 to each other in the real space, which is equal to the data 62. However, only by this explanation, it does not necessarily follow an image made from the data expanded by the method of FIG. 12 is equivalent to an image made from the data expanded by the method of FIG. 16. This is because filter processing has a relation to this in the frequency space. The fact that both the methods are equivalent to each other even when the filter processing is taken into consideration will be proved hereunder.

(Proof)

Let the data 58, 59, 60, 61, 62 and 63 be a, b, $a_O$, $b_O$, t and $t_O$ respectively, and let the Fourier transform of those data be A, B, $A_O$, $B_O$, T and $T_O$ respectively.

From FIG. 17, $$t = t_O = a_O + b_O \tag{24}$$

According to the linear property of the Fourier transform, $$T = T_O = A_O + B_O \tag{25}$$

Let the filter function in the frequency space be G. Multiplying both sides of the equation (25) by G, $$G \cdot T = G \cdot (A_O + B_O) = G \cdot A_O + G \cdot B_O \tag{26}$$

According to the linear rule of the Fourier transform, $$F^{-1}(G \cdot T) = F^{-1}(G \cdot A_O) + F^{-1}(G \cdot B_O) \tag{27}$$

The equation (27) expresses that the resultant data returned to the real space after the filter processing on the data t in the frequency space is equal to the resultant data obtained by the addition of two data returned to the Real space after the filter processing on the data $a_O$ and $b_O$ independent of each other. (Proof Finished.)

Even in the case where the data expanded by zero interpolation is used, it is possible to perform blur correction by the filter of H* expressed by the equation (23).

(3) Algorithm of Making High Resolution Image by Using Data Measured by Detector Array Without Shifting:

Description has been made above as to the algorithm for obtaining a high resolution image in the case where the data measured by detector arrays with shifting shown in FIG. 9 is used. High resolution image cannot be obtained by performing as shown in FIGS. 12 or 16 on the data measured by the detector arrays without shifting since the mutually opposite data have not the properly as shown in FIG. 11. However, the same high resolution image as in the case explained above in the item 2, (1) can be attained by data expansion processing by using interpolation.

Figure 18:
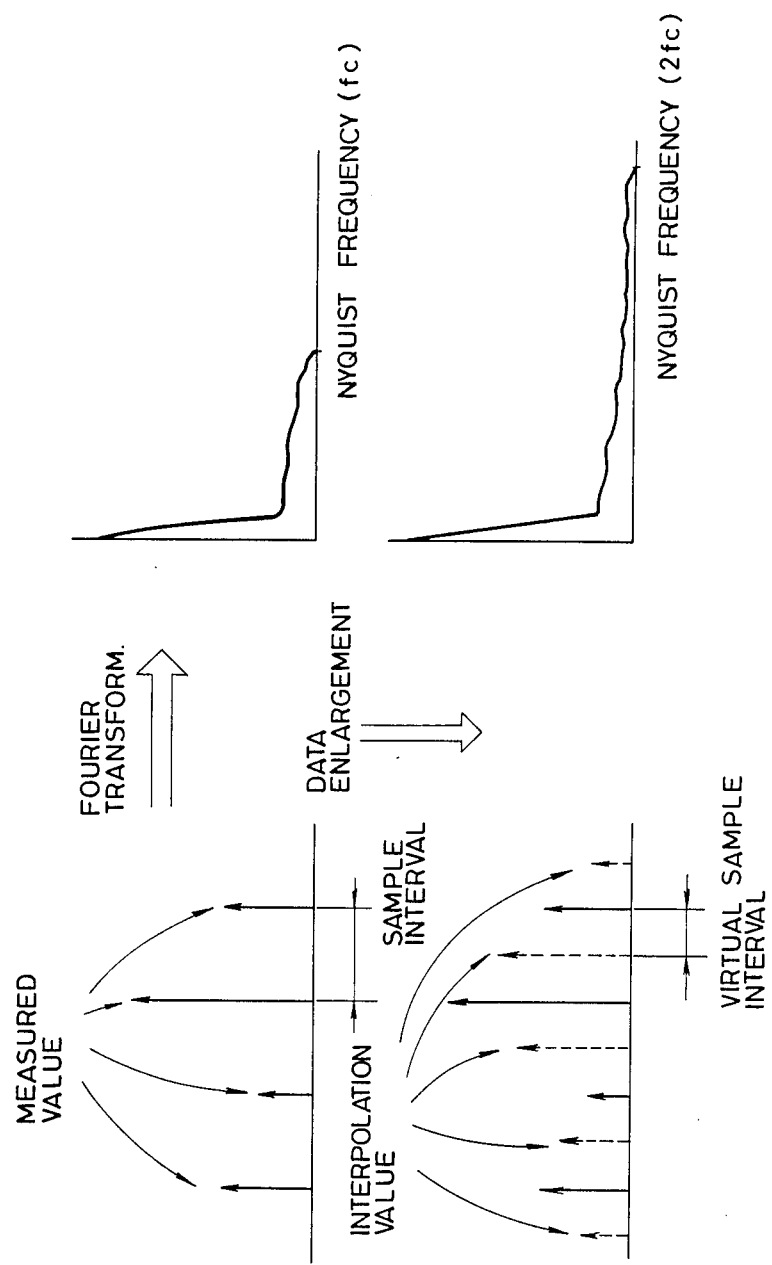
FIG. 18 is a diagram showing a method for expansion data by interpolation in accordance with another embodiment of the invention.

Assume that the data measured by parallel detector arrays are expanded by interpolation as shown in FIG. 18. FIG. 18 shows the case where two-point linear interpolation is employed as a most simple interpolating method.

In this case, the mean value of two adjacent detected values in interpolated between the two values and the data length is enlarged by twice. Assuming that the interpolating value is a value measured by the virtual detector, it is possible to consider that the sample interval is reduced to half by the data expansion. The Nyquist frequency of the expanded data is increased by twice of that of the initial data. As described above in comparison between the equations (6) and (7), the frequency components of the initial data smaller than twice the Nyquist frequency are within a positive phase transmission range in the detector aperture transmission characteristics. Therefore, a reconstructed image produced from the expanded data by using interpolation shows a high resolution property as compared with the case where data expansion is not performed.

Next, what kind of properties are provided in the expanded data owing to interpolation will be discussed and it will be shown the expanded data resulting from interpolation has properties similar to the expanded data resulting from the method of FIG. 12, whereby the theory for high resolution will be made clear.

Figure 19:
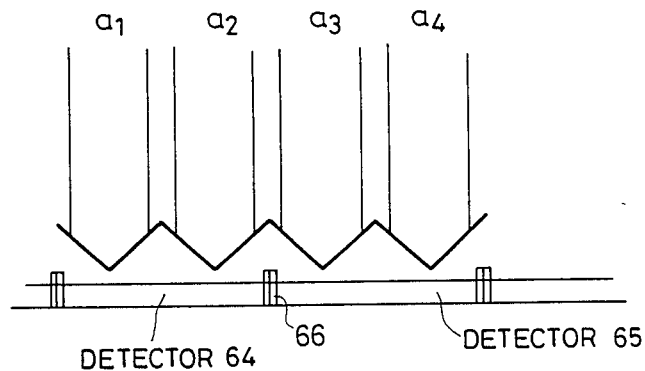
FIG. 19 is a diagram showing an example of a measurement by detecting elements having an aperture width with respect to the method of FIG. 18.

Let is be assumed four parallel X-ray beams $a_1$–$a_4$ are measured by detectors 64 and 65 as shown in FIG. 19. The beams $a_1$–$a_4$ have the width of $\frac{1}{2}$ of the detector aperture width.

Assuming that $a_1$–$a_4$ express X-ray intensity respectively, the detector 64 has the value $$a_1 + a_2 \quad (28)$$

and the detector 65 has the value $$a_3 + a_4 \quad (29)$$

The two-point linear interpolation value is obtained by the equations (28) and (29) as follows:

$$\frac{a_1 + a_2 + a_3 + a_4}{2} \quad (30)$$

Figure 20:
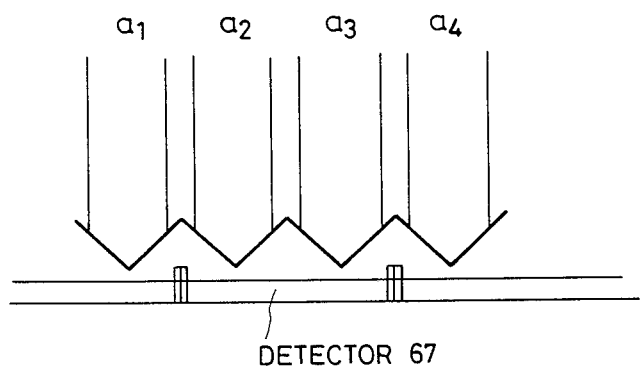
FIG. 20 is a diagram showing an example of a measurement by virtual detecting elements having an aperture width with respect to the method of FIG. 18.

The center of the detector 64 is in the boundary of $a_1$ and $a_2$, the center of the detector 65 is in the boundary of $a_3$ and $a_4$. The center of the virtual detector having the value of the equation (30) is in the boundary of $a_2$ and $a_3$. Since it is not natural to think this detector is twice as long in aperture width as the detectors 64 and 65, the virtual detector is regarded as the detector 67 of FIG. 20 if the aperture width of this detector is regarded as equal to the aperture width of the detectors 64 and 65. The detector 67 is shifted $\frac{1}{2}$ the detector width with respect to the detectors 64 and 65. This is the same as the positional relationship of a pair of data measured at an interval of 180° in the data measured by the parallel detector arrays with shifting as shown in FIG. 11. If actual measurement is performed at the position of the detector 67 of FIG. 20 by using the same detector elements as the detectors 64 and 65, a detected value is obtained as follows:

$$a_2 + a_3 \quad (31)$$

The equation (30) expresses the value made from the detectors 64 and 65 by interpolation, and the equation (31) expresses the value measured actually.

The error between these values in obtained by subtracting the equation (31) from the equation (30) as follows:

$$\frac{(a_2 + a_3) - (a_1 + a_4)}{2} \quad (32)$$

The equation (32) divided by the equation (31) gives the following equation (33):

$$\frac{1}{2}\left(1 - \frac{(a_1 + a_4)}{(a_2 + a_3)}\right) \times 100 \, (\%) \quad (33)$$

The data measured by the CT apparatus have high correlativity, and the equations (32) and (33) usually have very small values.

If the value obtained by interpolation is an approximation of the data measured by opposite detector arrays with shifting as described above, the processing of multiplication by filter H* expressed by the equation (23) must be effective, as discussed above in the item 2.(1). Actually, it is known that the multiplication by filter H* is effective for obtaining an extremely good image. Accordingly, it is understood that high resolution can be performed also in the case of using the expanded data obtained by interpolation in accordance with the same principle as in the case of using the expanded data obtained by the data expansion method of FIG. 12.

As the interpolating method, various methods such as four-point linear interpolation, spline approximation, etc. are effective other than two-point linear interpolation.

(4) The Case where Data Measured by Detector Array with Shifting is Expanded by Interpolation:

In the case where the processing of FIG. 18 is effected to the data measured by the detector arrays with shifting, the value obtained by interpolation can be regarded as an approximation of the value measured by the opposite detector arrays.

(5) Position to Perform Data Enlarging Processing:

The foregoing has been made mainly by using the data measured by the parallel detector arrays. If expressed by FIG. 6, the above description has been such that the data, after fan beam/parallel beam rearranging processing, is expanded by the processing of FIGS. 12, 16 or 18, and the data corresponds to a interpolation value obtained by interpolation process in consideration of the positional relationship of measuring points. And basically, multiplied by filter H*. Then the thus obtained data is transmitted to the parallel beam filter processor 21, thereby attaining high resolution. Accordingly, the meaning of the "data processing" is broadened so that it includes not only the processing shown in FIGS. 12, 16, or 18 but also the processing or multiplication by H*.

Figure 21A:
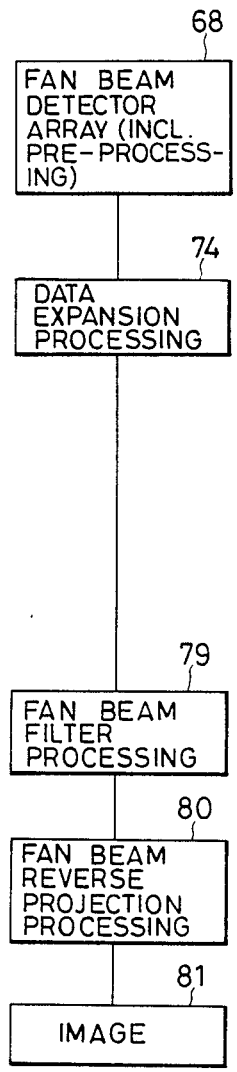
FIGS. 21A, 21B, and 21C are diagrams showing algorithms of high resolving power by the data expansion method to the present invention data in a fan beam CT.
Figure 21B:
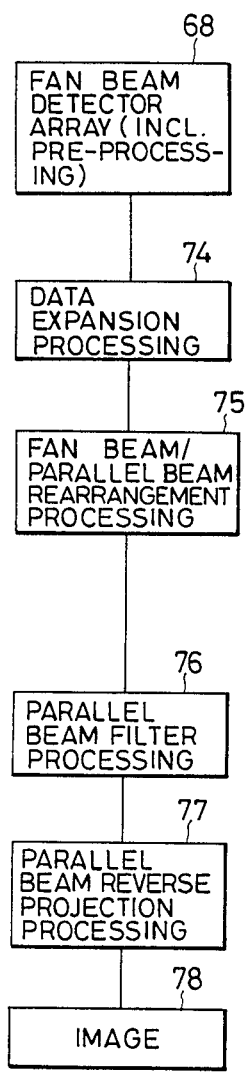
Figure 21C:
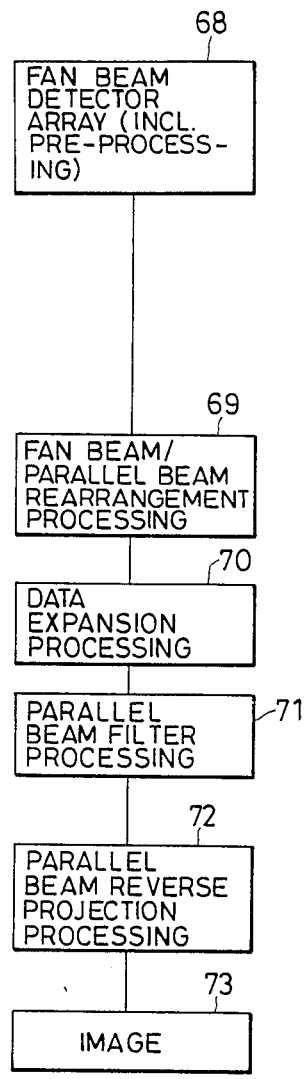

Practically, the position of data expansion processing is not always the above-mentioned position and it may be before the rearranging processing 20 as in FIG. 6 with the same result as in the foregoing case. FIGS. 21A, 21B and 21C show the combination of the processing of FIG. 6 with the data expansion processing. The above-mentioned methods of data expansion processing are applicable to FIGS. 21A, 21B and 21C.

In FIG. 21B, a data group which has been subject to the processing of FIGS. 12, 16 or 18 in fan beams is rearranged by fan beam/parallel beam rearranging processing 75 into a data group obtained by the processing of FIGS. 12, 19 or 21 in parallel beams.

In FIG. 21A, the fan beam filter correction back projecting processing is equivalent to the algorithm in which the rearranging processing is combined with the parallel beam filter correction back projecting processing, that is, the result according to the steps 79 and 80 in FIG. 21A is equivalent to the result according to the steps 75-77 in FIGS. 21B, and therefore, the two results are always the same as long as the same data is used for the two. Although the fact seems a little strange, the equivalency of the results of FIGS. 21A, 21B, and 21C has been proved by experiments.

The present invention will be described in detail with respect to four embodiments thereof hereunder.

Figure 22:
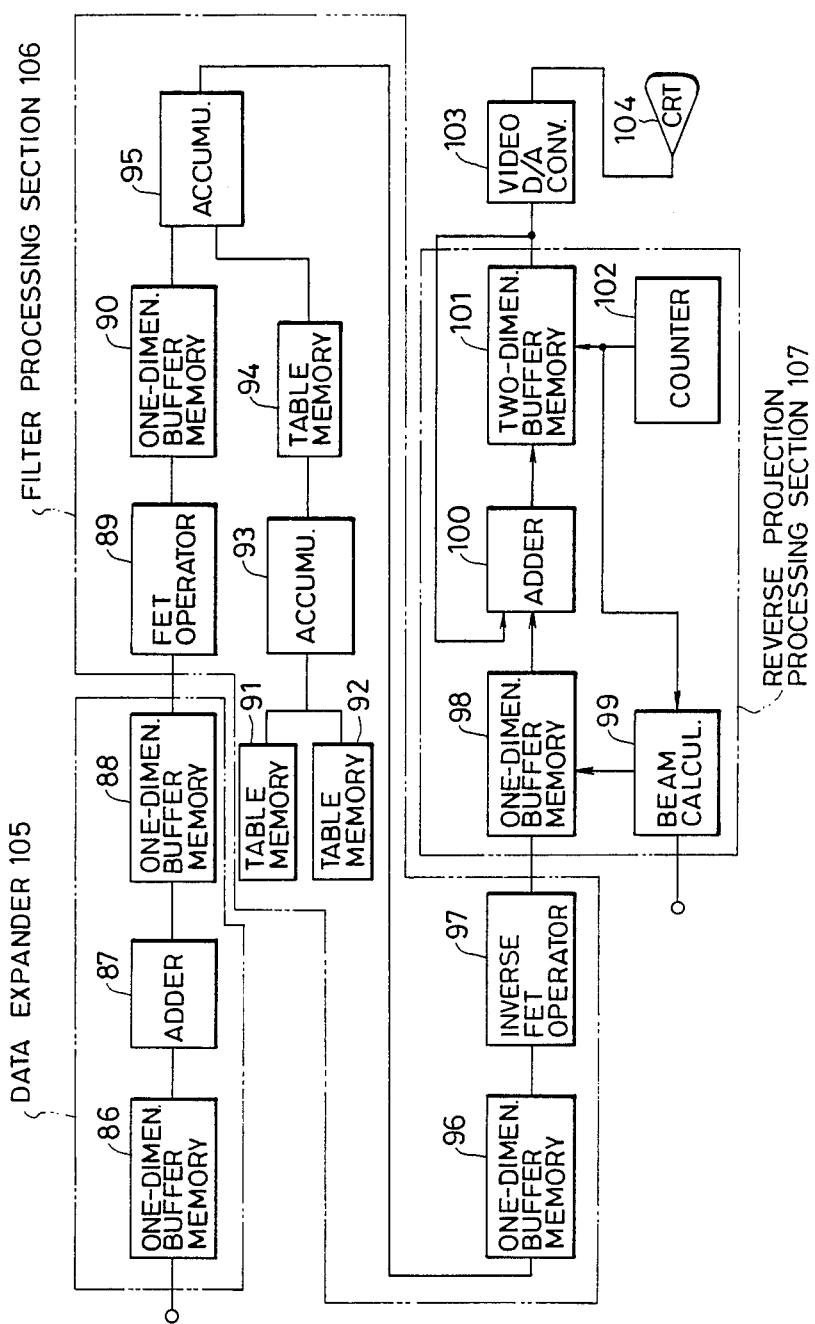
FIG. 22 is a block diagram showing an illustrative embodiment of tomographic image reconstruction circuitry in accordance with the present invention.

(1) FIG. 22 is a diagram showing a tomographic image reconstructing section of an apparatus for performing a filter correction back projecting method by using interpolation for data expansion and by using the product of the filter function $F(\omega)$ and $H^*(\omega)$ expressed by the equation (23).

The illustrated structure includes a data expander 105 for pre-processing in an ordinary filter correction back projecting method. A table memory 92 for storing a gain of the function $H^*(\omega)$ expressed by the equation (23) as well as a table memory 91 for storing a gain of an ordinary blur correction filter function are provided in a reverse filter processing section 106 so as to use the product of the two functions as a filter function. That is, a measured projection data $H(\lambda, \beta)$ expanded twice in data length by interpolation in expander 105. The expanded projection data is blur-corrected by the ordinary blur correction filter and $H^*(\omega)$ in the filter processing section 106. A tomographic image is formed in a back projection processing section 107, and a reconstructed image is obtained in a two-dimentional buffer memory 101. This reconstruction image is converted into video signals by a video D/A converter 103 and displayed on a CRT 104.

Although various methods such as Iagrange's interpolating method may be used as the interpolating method for the enlargement of the projection data, the simplest linear interpolating method is used here. The expanded data $H'(\lambda, \beta)$ is calculated so as to satisfy the following equations (34) and (35):

$$H'(2\lambda, \beta) = H(\lambda, \beta) \tag{34}$$

$$H'(2\lambda-1, \beta) = 0.5H(\lambda-1, \beta) + 0.5H(\lambda, \beta) \tag{35}$$

where
  $\lambda$: detector number (1, 2, 3, ..., m)
  $\beta$: X-ray tube number (1, 2, 3, ..., 360°)
  m: the number of detector elements The measured projection data $H(\lambda, \beta)$ is stored in the one-dimensional or linear buffer memory 86 by one for every position of the X-ray tube. The projection data stored in the one-dimensional buffer memory 86 is stored in the buffer memory 88 after the addition of the equation (35) is performed in the adder 87. Since the equation (34) expresses only transfer of data, the adder 87 does not perform addition with respect to equation (34) but only transfers the data from the memory 86 to the memory 88. The adder 87 performs this transfer of data and the processing of the equation (35) alternately.

The space filtration processing is performed with respect to the expanded projection data in the filter processing section 106. Digital high-speed Fourier transform is effected onto the data of the buffer memory by FFT operator 89 and the data is stored in the buffer memory 90. On the other hand, the multiplication of the gain of the ordinary blur correction filter function stored in a table memory 91 and the gain of the filter function $H^*(\omega)$ stored in a table memory 92 is performed by an multiplier 93 and stored in a table memory 94. The multiplication of the data stored in the memory 90 and the filter function stored in the memory 94 is performed by an multiplier 95, and the result is stored is a one-dimensional buffer memory 96. Inverse Fourier transform is effected onto the data stored in the buffer memory 96 by an inverse FFT operator 97, and the result is stored in a one-dimensional buffer memory 98.

Figure 23:
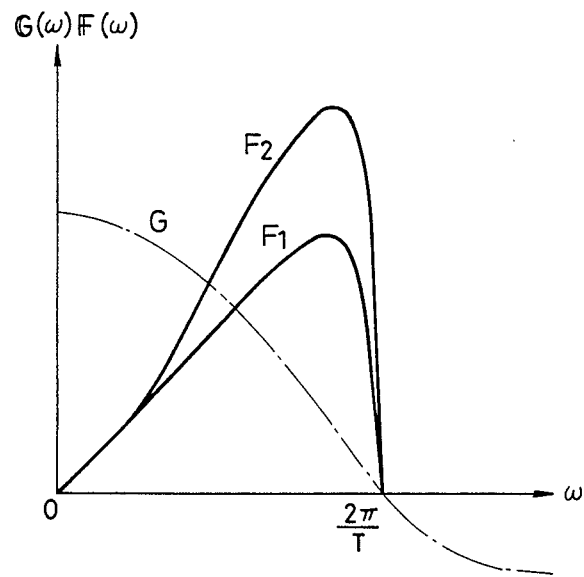
FIG. 23 is a diagram showing a sample aperture and a filter function in accordance with a further feature of the invention.

An ordinary blur correction filter function developed by Ramachandran, et. al. may be used as the filter function stored in the table memory 91. More preferably, a filter function having higher gain in a high-frequency band can be used for the purpose of high-frequency emphasis in the positive phase transmission area of aperture transmission characteristic. The examples are shown in FIG. 23, in which the Nyquist frequency of one projection data is the mean of $2\pi/T$ and O in the axis of the abscissa of FIG. 23 by T P. $F_1$ and $F_2$ respectively having high-frequency emphasis in the positive phase transmission area of G, are functions which become zero in the frequency of phase inversion position $2\pi/T$ or more. $F_2$ has high frequency emphasis more than $F_1$, and accordingly, the reconstructed tomographic image of $F_2$ is sharper than that of $F_1$, that is, more precise component in the object to be tested are computed. It is therefore possible that the improvement of special resoluting power according to this method is performed more effectively by using the filter function such as $F_2$. The degree of frequency emphasis has been confirmed experimentally, and the result shows the optimum characteristic was such that the inclination (the first order differential coefficient in the axis of frequency) of the Nyquist frequency $\pi/T$ and its vicinity was 1.5-3 times as much as the inclination of zero frequency and its vicinity and the value of function was zero in the area $2\pi/T$ or more where the detector aperture transmission characteristic was negative.

The back projection processing section 107 comprises a one-dimensional buffer memory 98, a beam calculator 99, an adder 100, a two-dimensional buffer memory 101, and a counter 102. The operation of this back projection processing section 107 is well-known and therefore the details thereof will be omitted. The back projection processing can have variations other than the above-mentioned construction. For example, there are "Fast Reconstruction Algorithm for Fan Beam CT System" (N. Yamagishi et al. The Institute of Electronics and Communication Engineers of Japan, Feb. 22, 1982, MBE 81-69), and "Fast Reconstruction Algorithm for Fan-Beam-CT-System" (I. Horiba et. al. The Journal of the Institute of Electronics and Communication Engineers of Japan, Apr. 25, 1985, vol. V68-D No. 4), etc.

(2) In the case where an image is constructed by the method in which the processing of FIG. 12 is used for the expansion of data, the adder 87 in FIG. 22 has to be replaced by the data expander which performs such processing as follows. When the projection data and the expanded data are $H(\lambda, \beta)$ and $H'(\lambda, \beta)$ respectively, this processing is such that the expansion of data is performed by transferring data expressed by the following equations (36) and (37):

$$H'(2\lambda, \beta) = H(\lambda, \beta) \tag{36}$$

$$H'(2\lambda-1, \beta) = H(\lambda_m - \lambda + 1, \beta + 180°) \tag{37}$$

The foregoing procesing must be performed for the projection angle up to 180° (not 360°).

(3) In the case where the processing of FIG. 16 is used as the data expanding processing, the adder 87 of FIG. 22 has to be replaced by a data expander which performs the processing expressed by the following equations (38) and (39):

$$H'(2\lambda, \beta) = H(\lambda, \beta) \tag{38}$$

$$H'(2\lambda-1, \beta) = 0 \tag{39}$$

This replacement makes it possible that an image of the same quality as can be obtained with the method described in the item 2.

(4) Even though the filter function $H^*(\omega)$ is not used respectively in the apparatus of each of Example 1-3, a good image can be obtained. Referring to FIG. 22, the table memories 91 and 92 and the multiplier 93 is removed and the gain of the filter function F1/F2 or the general blur correction filter function is stored in the table memory 94. In the conventional filter correction back-projecting method, more precise component than the sample interval in the detector array could not be resolved. When the sample interval was 0.74 (mm), the special resolving power was 0.75 (mm).

However, in the method of the first embodiment the resolving power was improved to 0.6 (mm) independent of the existence of the filter function $H^*(\omega)$, and in the methods of the second and third embodiments, it was improved to 0.5 (mm) independent of the existence of the filter function $H^*(\omega)$.

According to the present invention, it was possible to obtain high special resolving power finer than the detector width.

What is claimed is:

1. In an X-ray CT apparatus including an X-ray source for irradiating X-rays to an object to be tested; a radiant ray detector assembly for detecting the amount of X-rays transmitted through said object to be tested, said detector assembly having a plurality of detecting elements;

means for rotating said X-ray source and said detector assembly about an axis to produce detection signals corresponding to the amount of transmitted X-rays; filter means for filter processing said detection signal; and means for back-projecting the filtering resultant to thereby reproduce a distribution image of X-ray absorption in a cross-section of said object to be tested, the improvement comprising:

means for calculating interpolation values from said detection signals to form expanded signals having an elongated length so that the expanded signals are used for the filter processing, wherein said calculating means includes means for obtaining said interpolating values by processing sample points of said detection signals occurring at substantially facing positions as said X-ray source and said detector are rotated about said axis, and wherein sample values taken at mutually opposite positions are combined to obtain interpolated values.

2. The improvement as in claim 1, wherein each of said detecting elements has a predetermined width and wherein said detector assembly is shifted in the direction of rotation of said detector assembly so that a position on said detecting element apart from one end of said detecting element by one fourth of said predetermined width is in alignment with said axis and said X-ray source.

3. The improvement as in claim 2, wherein said calculating means includes means for obtaining said interpolating values, said interpolating values being obtained when said X-ray source and said detector assembly are rotated about said axis to mutually opposite positions.

4. The improvement as in claim 2, wherein said calculating means includes means for inserting zero values between the detection signals of two adjacent detecting elements.

5. The improvement as in claim 1, wherein said means for obtaining said interpolating values includes means for computing the mean value of two adjacent detected values and for inserting the mean value between the two adjacent detected values.

6. The improvement as in claim 1, wherein said calculating means includes means for obtaining said interpolating values by processing sample points of said detection signals, said means for obtaining said interpolating values including means for computing the mean value of two adjacent detected values and for inserting the mean value between the two adjacent detected values.

7. The improvement as in claim 1, wherein said calculating means includes means for obtaining said interpolating values, said interpolating values being obtained when said X-ray source and said detector assembly are rotated about said axis to mutually opposite positions.

8. The improvement as in claim 1, wherein said calculating means includes means for inserting zero values between the detection signals of two adjacent detecting elements.

9. The improvement as in claim 1 wherein said filter means includes means for blur correction filtering of the detection signals.

10. The improvement as in claim 9 wherein said detector includes an array of detectors where each detector has an aperture of a predetermined width and where said filter means has a characteristic such that the first order differential coefficient in the axis of frequency in the vicinity of the Nyquist frequency determined by the sample interval of the detection signal is increased 1.5-3 times with respect to the first order differential coefficient in the vicinity of zero frequency and the value of the characteristic is zero in the frequency region where the detector aperture transmission characteristic determined by the distribution of irradiating X-rays from the X-ray source and the distribution of sensitivity of detector aperture is negative.

* * * * *